United States Patent [19]

Olsen

[11] Patent Number: 5,670,156
[45] Date of Patent: *Sep. 23, 1997

[54] FELINE INFECTIOUS PERITONITIS VACCINE AND METHOD OF PREPARATION

[75] Inventor: Richard G. Olsen, London, Ohio

[73] Assignee: Parhelion Corporation, Columbus, Ohio

[*] Notice: The term of this patent shall not extend beyond the expiration date of Pat. No. 5,460,815.

[21] Appl. No.: 284,659

[22] PCT Filed: Feb. 18, 1993

[86] PCT No.: PCT/US93/01285

§ 371 Date: Aug. 18, 1994

§ 102(e) Date: Aug. 18, 1994

[87] PCT Pub. No.: WO93/15762

PCT Pub. Date: Aug. 19, 1993

[51] Int. Cl.⁶ .............. A61K 39/12; A61K 39/215; C12N 5/00; C12N 5/02
[52] U.S. Cl. .............. 424/221.1; 424/204.1; 435/240.2
[58] Field of Search .............. 424/221.1, 204.1; 435/240.2

[56] References Cited

U.S. PATENT DOCUMENTS

| | | | |
|---|---|---|---|
| 4,195,130 | 3/1980 | Hoshino et al. | 435/235 |
| 4,303,644 | 12/1981 | Davis | 424/89 |
| 4,434,157 | 2/1984 | Olsen | 424/89 |
| 5,043,157 | 8/1991 | Baldwin et al. | 424/89 |

FOREIGN PATENT DOCUMENTS

| | | |
|---|---|---|
| 0 310 362 A2 | 4/1989 | European Pat. Off. . |
| 0 411 684 A2 | 2/1991 | European Pat. Off. . |

*Primary Examiner*—Lynette F. Smith
*Attorney, Agent, or Firm*—Oblon, Spivak, McClelland, Maier & Neustadt, P.C.

[57] ABSTRACT

A vaccine for the prevention of disease caused by feline infectious peritonitis virus (FIPV) which comprises FIP viral precursor immunogens derived from in vitro produced cells persistently infected with FIPV. A method of producing FIP viral precursor immunogens is disclosed which comprises culturing in vitro FIP-persistently infected cells in a serum-containing growth medium, subsequently transferring and maintaining said cultured cells in a serum-free medium under conditions for a time adequate to accumulate FIP viral precursor immunogens shed from said cells, and then separating the cells from the supernatant containing the viral precursor immunogens. Any live virus present in the mixture is inactivated and the supernatant containing the FIP viral precursor immunogens is blended with a pharmaceutically-acceptable adjuvant in order to form the FIP vaccine disclosed herein.

17 Claims, 2 Drawing Sheets

FELINE INFECTIOUS PERITONITIS VACCINE AND METHOD OF PREPARATION

TECHNICAL FIELD

Feline infectious peritonitis (FIP) is a sporadic disease occurring unpredictably in domestic and wild Felidae. While FIP is primarily a disease of domestic cats, it has been diagnosed in lions, mountain lions, leopards, cheetahs, and the jaguar. Smaller wild cats that have been afflicted with FIP include the lynx and caracal, sand cat, and pallas cat. In domestic cats, the disease occurs predominantly in young animals, although cats of all ages are susceptible. A peak incidence occurs between 6 and 12 months of age. A decline in incidence is noted from 5 to 13 years of age, followed by an increased incidence in cats 14 to 15 years old. There is no significant sex predisposition. FIP occurs more frequently in purebred cats, presumably because these cats are kept more commonly in catteries or multiple cat households. The disease is world-wide in distribution.

FIP is caused by a type of coronavirus. Coronaviruses are pleomorphic, enveloped particles that average 100 nm in diameter and contain a single strand of RNA. Characteristic petal-shaped projections called peplomers protrude from the viral surface. In many species of animals, coronaviruses have a relatively restricted organ tropism, infecting the respiratory and/or gastrointestinal systems. Following oral infection, the viruses have an affinity for the mature apical columnar epithelium of the villi in the duodenum, jejunum, and ileum.

The coronaviruses that infect cats have been divided into those that cause FIP (FIPVs) and those that induce subclinical to severe enteritis (the feline enteric coronaviruses, or FECVs). The FIPVs differ from the FECVs in their ability to escape from the gastrointestinal tract and spread to replication sites in distant tissues. FIPVs and FECVs may represent pathogenetic variants of a single coronavirus type. Alternatively, FIPVs may arise periodically as mutants of FECV strains.

FIPV, transmissible gastroenteritis virus (TGEV) of swine, canine coronavirus (CCV), and human respiratory tract coronaviruses of the 229E group comprise an antigenic cluster of closely related viruses within the Coronaviridae group. The major structural polypeptides of FIPV, TGEV, and CCV are so similar antigenically that some consider these three viruses as host range mutants rather than individual viral species.

The name, feline infectious peritonitis, refers to the principal form of the disease, an inflammatory condition of the visceral serosa and omentum. A reported second form of FIP is characterized by granulomatous involvement of parenchymatous organs such as the kidneys, mesenteric lymph nodes, liver, pancreas, central nervous system (CNS) and spine, and the uveal tract of the eye. The granulomatous form of FIP is called "dry" or "noneffusive" because there is no inflammatory exudation into the body cavities. Classical FIP, which comprises about three-fourths of the cases, is termed "wet" or "effusive." A third form of FIP combines characteristics of both the effusive and noneffusive varieties.

The clinical course of effusive FIP lasts from 1 to 6 weeks or sometimes longer. The onset of disease is heralded by the appearance of a chronic, fluctuating fever. Associated with the fever there is usually a progressive decline in weight, activity, and appetite. Terminally, the cats go into shock and die. Peritonitis is seen in over 90% of the cats with effusive FIP and pleuritis in around 40% of the cases. Involvement of other organs, such as the eyes and CNS, is clinically apparent in only 10% of the cats with effusive disease, although a somewhat higher proportion may have clinically silent lesions in these and other non-serosal sites.

Cats with noneffusive FIP are ordinarily ill for 1 to 12 weeks or longer. As with the effusive form, a chronic fluctuating fever accompanies the disease. There also is a progressive decline in general body condition and appetite. Added to these features, however, are signs referable to specific organ systems. Peritoneal cavity lesions are found in 50% of cats with noneffusive FIP and pleural cavity lesions in 10%. Noneffusive FIP differs from the effusive form in that there is a high incidence of ocular or CNS involvement. Approximately one-third of cats with noneffusive FIP demonstrate signs referable to the CNS, and a similar number have clinically-apparent ocular disease.

The precise routes by which FEPV enters the body are not known. FIPV is a heat-labile virus, being inactivated at room temperature within 24 to 48 hours. It is unlikely that cats with FIP are the only source of FIPV in nature. Similarly, contaminated fomites are an unlikely source of infection, given the short stability of FIPV outside the host. In most cases, transmission of virus probably occurs via the feces and, less commonly, the urine or oronasal secretions of asymptomatic carriers. To explain the sporadic and random incidence of the disease, carrier cats would have to shed the virus either intermittently or at exceedingly low levels.

Queens that are asymptomatically infected with FIPV may infect their offspring in-utero or in the neonatal period. Kittens infected in-utero may be born sick or may show no signs of disease. However, some asymptomatic infected kittens may develop FIP at a later time if their immune responsiveness becomes impaired.

Concurrent infection with feline leukemia virus (FeLV) has been reported in cats infected with FIPV. The mechanism by which FeLV infection potentiates the incidence of FIPV is not specifically known, although controlled observations reported in the literature have led to the assumption that FeLV infection in some way interferes with established FIPV immunity. The mechanism of this interference has been speculated to involve any number of generalized immunosuppressive effects that have been described in connection with persistent FeLV infection, which dispose cats to intercurrent or opportunistic infections.

Specific pathogen-free (SPF) kittens that are exposed to FIPV by oral or intratracheal instillation react serologically in several ways. Some kittens do not develop any signs of infection after prolonged exposure, and they remain antibody-negative. Kittens which are infected but do not develop signs of illness demonstrate a plateau-shaped antibody response, while kittens that develop FIP demonstrate a progressive antibody titer rise. In both groups of infected kittens, the presence of virus-neutralizing antibodies tends to correlate with immunofluorescent antibody (IFA) titers. Sometimes, however, an infected cat will develop only virus-neutralizing antibodies, and IFA titers will be negligible. Difficulty is encountered in the interpretation of serologic responses due to antigenic similarity between FIPV and the non-FIP-inducing coronaviruses (FECV), and the ubiquitousness of FECV infection in nature. About 25% of free-roaming cats have been or remain infected with FECV, with infections especially prevalent in catteries and multiple cat households. Infection with FECV results in the production of coronaviral antibody that is, at present, serologically indistinguishable from that induced by infection with FIPV, CCV, or TGEV.

Antibody formed as a result of FECV infection does not protect the cat from later challenge with a virulent strain of FIPV. In fact, this antibody sensitizes the cat to later challenge, accelerating the disease process induced by the virulent FIPV.

Initial attempts to immunize cats with TGEV of swine to provide protection against FIP have proven unsuccessful, although immunization of piglets with FIPV is known to invoke antibody production against TGEV. To date, immunization with killed FIPV also has proven uniformly unsuccessful. The immunity derived from autologous killed vaccines almost always renders cats more susceptible to challenge with the virulent living virus, and the disease that results usually is more severe and fulminating. Vaccination with attenuated FIPV also has proven unsuccessful as evidenced by a lack of such products commercially. In this regard, reference is made to Gerber et al, "Protection Against Feline Infectious Peritonitis by Intranasal Inoculation of a Temperature-Sensitive FIPV Vaccine", Vaccine, Vol. 8, pp 536–542 (December 1990); and U.S. Pat. Nos. 4,293,653, 4,303,644, and 4,571,386.

Gerber et al disclosed a feline infectious peritonitis virus vaccine derived from a virulent strain (DF2-FIPV) adapted to tissue culture on the Norden Laboratories Feline Kidney (NLFK) cell line (Norden Laboratories, Lincoln Nebraska USA). The virus was attenuated by passage on NLFK cells for 99 passages. The last passage was made temperature sensitive by exposure to ultraviolet irradiation. The temperature sensitive FIPV was then propogated on NLFK cells for 8 more passages and lyophilized. This method does not involve a persistently infected cell line. The NLFK cells are infected with the virus after every passage. The present invention is neither a live attenuated virus nor a killed virus vaccine. It is based on immunogens present in the supernatant of cultured cells which are persistently infected with FIPV. Various methods for propagation of feline infectious peritonitis virus by means of tissue culture have been reported (U.S. Pat. Nos. 4,195,130; 4,293,653; and 4,303,644), however, none discloses a persistently-infected cell line.

The prognosis for cats with FIP is poor, since there is currently no effective treatment to terminate the viral infection. Some treatment regimens allow short-term remissions in carefully selected patients. The best patients for palliative therapy are those cats with FIP that are not infected with FeLV, are in good physical condition, maintain a good appetite, and have no evidence of severe anemia or neurologic signs. Unfortunately, few cats with FIP are presented early enough in the course of disease to meet these criteria, and most afflicted cats will die within 1 to 16 weeks.

Sources of additional information concerning FIP include Olsen et al., Comparative Pathobiology of Viral Diseases, vol.2, pp. 115–136, CRC Press, Inc., Boca Raton, Fla. (1985), and references cited therein; and Norden News, Autumn 1989, pp. 15–19, Lincoln, Nebr., the disclosures of which are incorporated expressly herein by reference.

DISCLOSURE OF THE INVENTION

One object of the present invention is to provide a vaccine for the prevention of disease caused by feline infectious peritonitis virus (FIPV). Such vaccine comprises FIP viral precursor immunogens derived from in vitro produced cells persistently infected with FIPV. Preferred in the production of viral immunogens forming the vaccine of the present invention is the Crandall Feline Kidney (CRFK) cell line.

Thus, a second aspect of the invention comprises FIP-infected Crandall Feline Kidney cell line, deposited at the American Type Culture Collection (ATCC), Rockville, Md., on Sep. 23, 1992, and granted Accession No. CRL 11137.

A third aspect of the invention relates to a method of producing FIP viral precursor immunogens, which comprises culturing in vitro FIP-persistently infected cells in a serum containing growth medium, subsequently transferring and maintaining said cultured cells in a serum-free medium under conditions and for a time adequate to accumulate FIP viral precursor immunogens shed from said cells, and then separating the cells from the supernatant containing the viral precursor immunogens. The supernatant containing the FIP viral precursor immunogens is then treated with an agent to inactivate any live virus that may be present in small amounts, and blended with a pharmaceutically-acceptable adjuvant in order to form the FIP vaccine disclosed herein.

BEST MODE FOR CARRYING OUT THE INVENTION

Figure 1A:
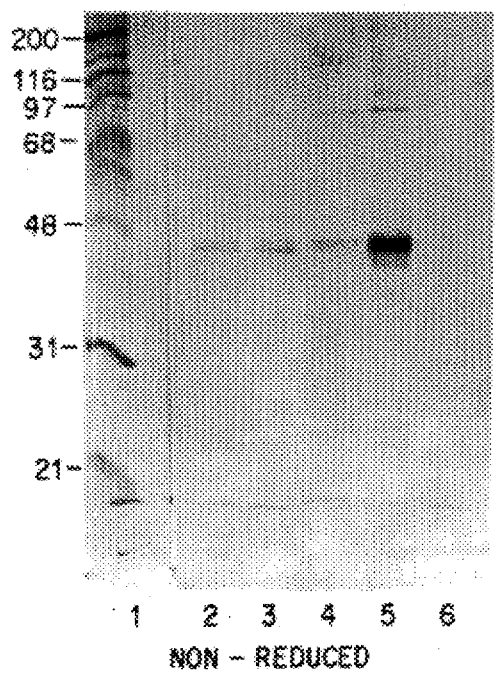
FIGS. 1A and B are photographs of a western blot of the FIPV immunogens under non-reduced and reduced conditions.

The vaccine of the present invention effectively protects cats against disease associated with FIPV. Furthermore, inoculated cats do not serve as carriers of the disease. This protection, coupled with the fact that the vaccine is free of live virus underscores highly significant advantages conveyed by the inventive vaccine. Because the vaccine requires neither living nor dead virus, but is rather a product of viral-infected cells (i.e., viral precursor immunogens), it is not only extremely effective but essentially risk-free as well.

The inventive FIP vaccine can be combined with vaccines effective against other feline diseases without prejudicing its efficacy. Other vaccines which may be combined with the instant vaccine include, for example, vaccines against feline leukemia virus (FeLV), feline sarcoma virus (FeSV), feline panleukopenia virus (FPV), feline calicivirus (FCV), and feline herpesvirus I (FHV-I), which causes feline viral rhinotracheitis.

The viral precursor immunogens derived from the persistently-infected cells are proteins or protein precursors (i.e., unassembled viral proteins) associated with FIP. With reference to the method of collecting the viral precursor immunogens, the first step requires the selection of a cell line capable of persistent infection with FIPV, but for which FIPV is noncytotoxic. Further, it is desirable not to sacrifice the cell line for the sake of harvesting the viral precursor immunogens. Thus, the cell line of choice should not only be capable of persistent infection with FIP, but should also be amenable to the harvesting of viral precursor immunogens followed by recycle to the process for subsequent rounds of growth and harvesting.

The infected cells first are placed in a serum-containing growth medium for culture which comprises a conventional serum-free growth medium having added thereto an appropriate quantity of animal serum, such as fetal bovine serum. Appropriate serum-free media include McCoy's 5a medium and RPMI 1640 medium (Gibco, Grand Island, N.Y.), and like conventional media. To such a serum-free medium are added appropriate quantities of serum and antibiotics in conventional fashion. The cells are cultured, with additional serum optionally added from time to time, preferably until the cells have reached saturation density in the volume of medium used. Conventional growth conditions are maintained which are well known in the art.

The next step of the process comprises transferring the cultured persistently infected cells to a serum-free growth medium of composition desirably substantially the same as that used in the culturing step, except that no serum is used or added during this subsequent step. Once the cells are placed in a serum-free medium they apparently cease their normal growth cycle and virtually all viral production is arrested. As a result of the severe stress to which the cells are subjected in serum-free medium, an abundance of viral precursor immunogens (and possibly additional cell matter) are shed from the cells in substantial quantities. It is this material, rather than killed virus or attenuated live virus, that is essential for a vaccine of the present invention.

The supernatant, comprising the serum-free medium containing viral precursor immunogens, is then separated from the persistently-infected cells by conventional separation techniques including, for example, centrifugation. The separated cell line can then be recycled to the culturing step of the process, with serum-containing growth medium. The determination of FIP viral precursor immunogens separated from the harvested infected cell lines can be conveniently determined by dot-blot analysis.

The FIP viral precursor immunogens may be lyophilized for storage or can be converted into a vaccine immediately. If lyophilization is the technique of choice, the viral precursor immunogen powder can be stored in such form or, if preferred, can be resuspended and stored at very low temperatures (e.g., $-67.8°$ to $-126.7°$ C.).

In order to convert the FIP viral precursor immunogens into a vaccine of the present invention low titers of live virus in the supernatant must first be inactivated, for example by treatment with β-propiolatone, formalin, glutaraldehyde, binary ethylene amine or heat. The inactivated mixture is then diluted, preferably to minimal effective amount, and blended with a pharmaceutically-acceptable adjuvant. Conventional adjuvants include complete or incomplete Freund's adjuvant, aluminum hydroxide, Quil A, EMA, DDA, TDM-Squalene, lecithin, alum, saponin, and such other adjuvants which are well known in the art, and also mixtures thereof.

The vaccine, as prepared or in combination with other feline vaccines or inoculants, can be used to inoculate both domestic and wild Felidae for the prevention of disease associated with FIPV. Viral precursor immunogen units per dosage are administered to cats by the conventional routes of administration, e.g., parenteral inoculation, including subcutaneous and intramuscular vaccination, or oral administration. Parenteral inoculation is the preferred route of administration.

Both kittens and adult cats can be vaccinated with the vaccine and thereby receive full protection from infection. The preferred minimum age of the kitten for inoculation, as with most other vaccines, is at about 8 weeks when the kitten has been weaned and maternal antibody has disappeared. A suggested time range for vaccination, thus, encompasses the period of 6 to 12 weeks of age.

The following examples illustrate the manner in which the present invention has been practiced, but should not be construed as limiting. All units herein are in the metric system unless otherwise expressly indicated, and all references cited herein are expressly incorporated by reference.

EXAMPLE 1

Crandall Feline Kidney (CrFK) cell line was infected with feline infectious peritonitis virus (ATCC-VR-867; Dahlberg strain) diluted 1:100 and incubated 1 hour at 37° C. The cells were incubated at 37° C. until cytopathic effect (CPE) was maximal.

Fresh growth medium (GM), comprising Eagles Minimum Essential Medium (MEM) containing Earles Salts and supplemented with 10% heat-inactivated fetal bovine serum, antibiotic mixture, and 2 mM glutamine, was added to the flask and incubated at 37° C. The cultures were examined every three days and small islands of cell growth were observed. Fresh GM was added until the cells reached confluency. Cultures then were maintained by the addition of 0.025% trypsin, to remove and dissociate cells from the flask into single cells, and passaged to other flasks. The cells also were grown on cover slips and examined for virus production using the indirect immunofluorescent antibody (IIFA) technique with FIP monoclonal antibody as the primary reagent. Cell lines were monitored each passage for virus production and were frozen for storage every five passages.

IIFA was conducted according to the following procedure:

1. Cover slips were sterilized by steam sterilization in glass Petri dishes.

2. CrFK-FIP cells were added to cover slips in GM and incubated until confluent, usually 48 hours.

3. Medium was decanted and cells washed with Dulbecco's calcium-magnesium-free phosphate-buffered saline (CMF-PBS).

4. The dishes were filled with −20° C. acetone and fixed in the freezer for 10 minutes. The acetone was removed, and the cells were air-dried and either used immediately or stored "dry" at −20° C.

5. Cover slips were flooded with FIP monoclonal antibody, diluted 1:1000, and incubated for 30 minutes at 37° C. in a humidified atmosphere.

6. The cells were washed 3 times with CMF-PBS at 5 minutes per wash, dried, and secondary reagent was added.

7. Rabbit anti-mouse IgG conjugated with fluorescein isothiocyanate (FITC) diluted 1:40 comprised the secondary reagent.

8. The secondary reagent was incubated and washed as described in steps 5 and 6.

9. Following the last wash, the cover slips were dipped in distilled water, air-dried, and mounted cell-side-down on a glass microscope slide in a 1:1 mixture of glycerin:CMF-PBS.

10. The cells were examined with an ultraviolet epifluorescent microscope with appropriate exciter and barrier filters.

11. Positive cells were identified by granular apple-green cytoplasmic fluorescence.

12. Noninfected CrFK cells were utilized as controls.

EXAMPLE 2

For vaccine production, virus-tested cells were transferred to large plastic T-flasks (75 or 250 ml) in GM and incubated at 37° C. until confluent. The medium was replaced with serum-free GM and incubated at 37° C. for 72 hours. Samples were removed for testing at 24 and 48 hours. At 72 hours, the medium was collected and centrifuged to remove cellular debris. Clarified supernatants were concentrated 10 x by dialysis with polyethylene glycol 1000 (Aquacide III, Calbiochem, La Jolla, Calif.) at 4° C. The 10 x concentrated supernatant was tested for FIP antigens by dot-blot analysis and frozen at 85° C.

The dot-blot analysis was conducted as follows:

1. 1 x and 10 x vaccine preparations were tested.

2. 20 microliter samples were pipetted onto strips of nitrocellulose paper (pore size 45 micrometers) and air-dried. The following samples were used:

◊ 24 hours
◊ 48 hours
◊ 72 hours (1×)
◊ 72 hours (10×)
◊ Serum-free MEM only
◊ Serum-free MEM from noninfected CrFK cells incubated 72 hours
◊ FIP virus (1:50 dilution)

3. Strips were incubated with 5% bovine serum albumin (BSA) at 5 g/80 ml PBS: 20 ml Tween 20 (Sigma Chemical, St. Louis, Mo.) for one hour at 37° C.

4. Strips were incubated in FIP monoclonal antibody solution at 1:200 dilution for one hour at 37° C.

5. Strips were washed 3 times for 10 minutes per wash on an orbital platform in 5% BSA-Tween 20 wash.

6. Strips were incubated with secondary reagent, Staphylococcus protein A conjugated to alkaline phosphatase, diluted 1:500. Strips were placed in BCIP/NBT substrate comprising 1 ml BCIP concentrate, 1 ml NBT concentrate, and 10 ml Tris buffer (Kirkegaard & Perry Labs, Inc., Gaithersburg, Md.) and the color was developed to desired intensity, usually between 5 and 10 minutes.

7. The reaction was stopped by dipping the strips in distilled water.

8. The strips were air-dried and sealed in tape.

9. The strips were visualized for dark blue/black staining when compared to negative and positive controls.

Inactivation of live virus or attenuated live virus present in the mixture was accomplished by freshly preparing beta-propiolactone at a dilution of 1:100 in distilled deionized water and adding it to a virus suspension at a final concentration of 1:1200, followed by incubation at 37° C. for 2 hours. The inactivated vaccine was tested for infectious virus by titrating inactivated sample on susceptible CrFK cells. Results were considered negative if no vital cytopathology was noted by daily observation of infected cells and appropriate controls.

EXAMPLE 3

Western blot characterization of FIPV persistently infected CrFK cells:

Sodium dodecyl sulfate-polyacrylamide gel electrophoresis (SDS-PAGE) of the FIPV immunogens was performed using a modification of the Laemmli system (Laemmli, U: Cleavage of structural proteins during the assembly of the head of bacteriophage T4. Nature 227:680–681, 1970). SDS-PAGE was conducted under constant current and reducing or non-reducing conditions, using a 3.5% stacking gel and a 10% running gel. Electrophoretic transfer of the proteins from SDS-PAGE gels to Immobilon-P (Millipore) transfer membranes was conducted by the method of Towbin, et al (Towbin, H, Staihlin, T, and Gordon, T: Electrophoretic transfer of proteins from polyacrylamide gels to nitrocellulose sheets: procedure and some applications. Proc. Nat. Acad. Sci. 76: 4350–4355, 1979). The blots were immunostained using a polyclonal serum from a cat challenged with the Dahlberg strain of FIPV as the primary antibody. The secondary antibody was rabbit anti-cat immunoglobulin conjugated with alkaline phosphatase.

Figure 1B:
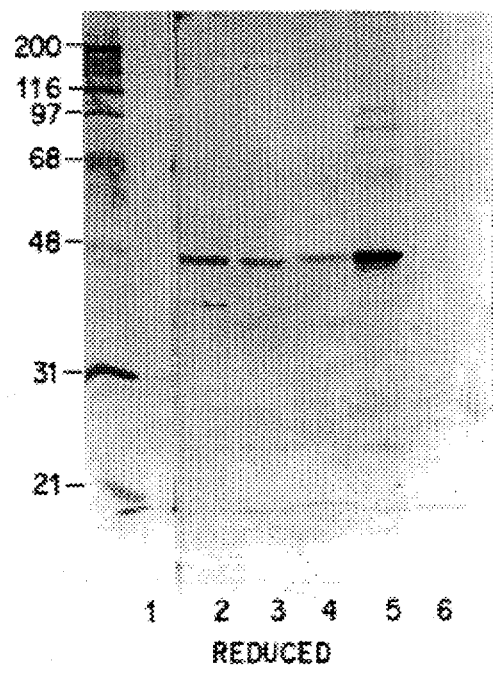

FIG. 1 is a photograph of a Western blot of the FIPV immunogens, under non-reduced and reduced conditions, from left to right, the first lane is a molecular weight marker control, lane two is Parhelion viral immunogens (10-14-92) —polyethylene glycol precipitated, lane three is Parhelion viral immunogens (10-26-92)—polyethylene glycol precipitated, lane four is Parhelion viral immunogens (CRFIP 27K)—non-precipitated, lane five is a virulent FIPV isolate (FIPV5) and lane six is a CrFK cell control.

Virus specific protein bands, S (200 kDa), N (46 kDa), and M (28 kDa) are visible in lane 5 for the virulent FIPV isolate. Additional bands (70 kDa and 97 kDa) are evident in this lane which are not evident in lanes 2, 3 and 4 for the Parhelion FIPV immunoblots. Virus specific bands (180–190 kDa) are evident for the Parhelion FIPV immunogens but not detectable in the immunoblot of the virulent virus (lane 5). These could be cleavage products of the S protein which are present in the FIPV persistently infected cell line but not present in the viral fluids of the virulent FIPV5.

Figure 2:
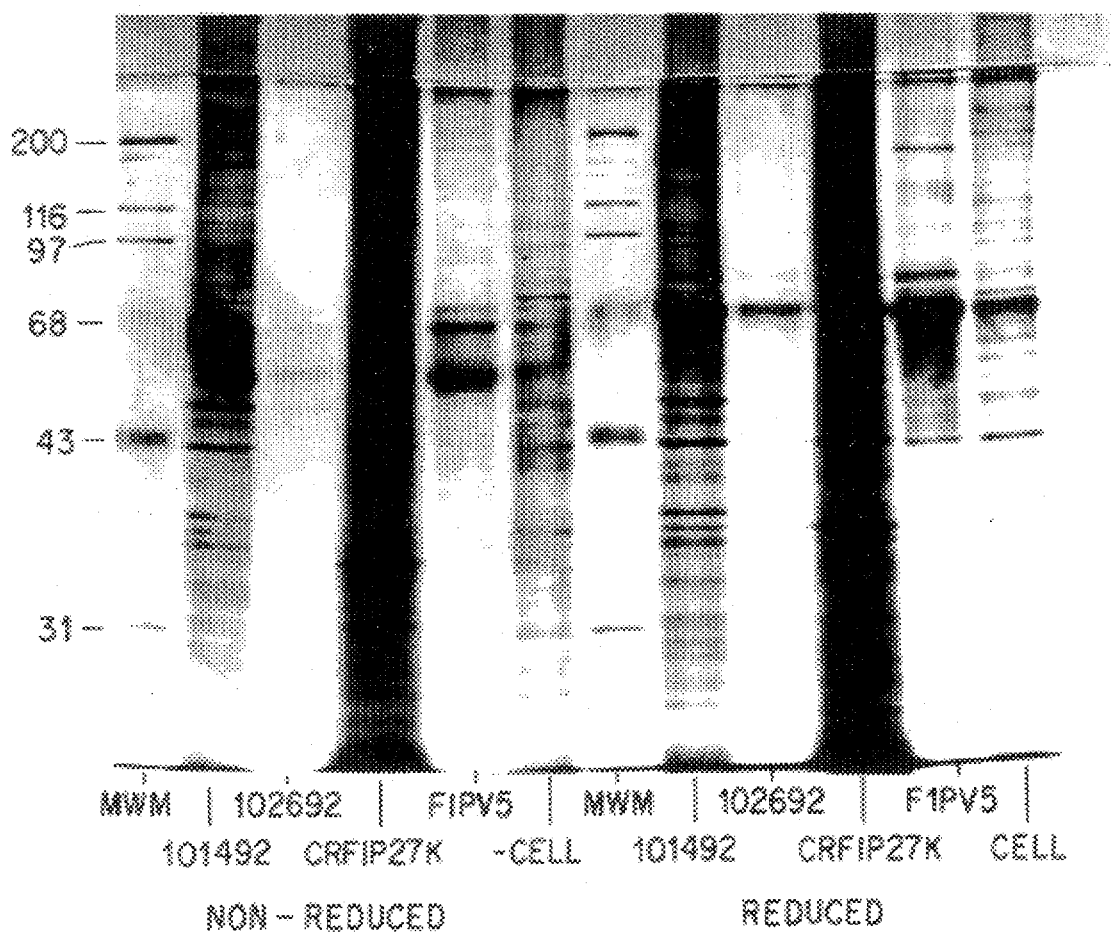
FIG. 2 is a photograph of a silver stain of the unblotted FIPV immunogens under non-reduced and reduced conditions.

For comparative purposes, a silver stain of the unblotted FIPV immunogens under non-reduced and reduced conditions is presented in FIG. 2. From left to right, the first lane is a molecular weight marker control, lane two is Parhelion viral immunogens (10-14-92)—polyethylene glycol precipitated, lane three is Parhelion viral immunogens (10-26-92) - polyethylene glycol precipitated, lane four is Parhelion viral immunogens (CRFIP 27K) - nonprecipitated, lane five is a virulent FIPV isolate (FIPV5) and lane six is a CrFK cell control. This half of the gel was run under non-reduced conditions, while the same samples were run under reduced conditions as described on the right side of the picture.

EXAMPLE 4

Twelve SPF cats were used for the immunization and protection studies, in accordance with the following protocol:

◊ Group A: 4 cats, oral administration of vaccine (1.0 ml);

◊ Group B: 4 cats, subcutaneous administration of vaccine (1.0 ml) comprising 1:1 mixture of 10 x vaccine concentrate with Seppic ISA50 adjuvant (Monatide, Paris, France);

◊ Group C: 4 cats, nonimmunized as controls.

A 3-dose regimen and serum sampling protocol was effected:

◊ Week 0: Condition cats for 2 weeks;
◊ Week 2: Prebleed cats for 1.0 ml serum;
◊ Week 3: Prebleed cats for 1.0 ml serum and administer first vaccine dose;
◊ Week 4: Trial bleed cats and administer vaccine dose 2;
◊ Week 5: Trial bleed cats and administer vaccine dose 3;
◊ Week 6: Trial bleed cats and administer initial virus challenge;
◊ Week 14: Trial bleed cats and administer second virus challenge;
◊ Week 16: Bleed cats and necropsy.

Summaries of the clinical course and histopathologic findings are set forth in the following tables:

TABLE 1

Summary of Clinical Course

| Group | Cat # | Clinical Signs | Survival dpc* |
|---|---|---|---|
| A | GU3 | Anorexia, fever, thin, weak 23 dpc$_2$ | 79 |
| A | GF4 | None, healthy | alive |
| A | GJ1 | None, healthy | alive |
| A | GU4 | None, healthy | alive |
| B | GA2 | None, healthy | alive |
| B | GB3 | None, healthy | alive |
| B | GJ2 | [Anesthetic death] | xxx |
| B | GM1 | None, healthy | alive |
| C | GM2 | Anorexia 11 dpc$_1$ | 17 |
| C | GN6 | Anorexia 18 dpc$_1$ | 36 |
| C | GR5 | Anorexia | 53 |
| C | GP5 | Anorexia 8 dpc$_1$; recovered 13 dpc$_1$; did not receive 2nd challenge | alive |

*dpc = days post challenge (1 and 2)

TABLE 2

Summary of Histopathologic Findings

| Cat # | Euthanized | Pathological Lesions |
|---|---|---|
| GM2 | 17 dpc$_1$ | Effusive peritonitis; multifocal necrohistiocytic inflammation of all visceral organs; villous atrophy, ileum; erythroid hypoplasia, myeloid hyperplasia |
| GN6 | 36 dpc$_1$ | Effusive peritonitis, multifocal pyogranulomatous inflammation of all visceral organs, brain, and eye; erythroid hypoplasia; myeloid hyperplasia |
| GR5 | 17 dpc$_2$ | Effusive peritonitis; multifocal to coalescing pyogranulomatous inflammation of all visceral organs, brain, and eye; villous atrophy, ileum; transmural granulomatous ileitis; erythroid hypoplasia; myeloid hyperplasia |

Animals were observed daily for clinical signs of FIP. As the foregoing data reveal, after the first challenge, three of the four cats in the unvaccinated control group showed clinical signs of FIP. These three cats were euthanized, all in moribund condition, two following the first challenge and the third following the second challenge. Of the vaccinated cats, three of the four cats in Group A and all of the cats in Group B (excepting cat GJ2, which succumbed to anesthesia) remained healthy throughout the study.

In the Group C control cats, lesions typical of FIP were found in a variety of organs. All three of the euthanized cats had effusive peritonitis and multifocal necrotizing to granulomatous lesions in liver, kidney, and lung. Cat GM2 had a peracute histiocytic response, while cats GN6 and GR5 evidenced mainly a pyogranulomatous response, more typical of spontaneous FIP. In addition, pyogranulomatous lesions were present in the brains and eyes of the two cats with more prolonged disease, but were absent from the animal which had died acutely. The intestines of all three cats showed mild to severe dilatation of intestinal glands by necrotic debris, leukocytes and mucous, in both the small intestine and colon. In two cats, severe villous atrophy was evident in the ileum; transmural granulomatous enteritis was present in the third cat.

Thus, inoculation of cats with FIPV accurately recapitulates the pathologic features of severe spontaneous disease, with infected cats developing typical pyogranulomatous lesions. Additionally, this FIP strain induces intestinal lesions which are not dissimilar to coronaviral enteritides in other species, but which have not been associated with spontaneous FIP.

Accordingly, the foregoing data demonstrate that the inventive vaccine provides protection against multiple exposures to a highly virulent FIPV. In addition to being nearly 100% effective, the inventive vaccine possesses significant advantages over traditional modified live vaccine approaches in that there is no risk of shedding infectious virus particles, there is no possibility of reversion to a virulent strain, and the vaccine can be readily mixed with other inactivated vaccines.

Immunogen(s) produced by cells persistently infected with all known strains of FIPV can also stimulate an adequate immune response in cats so as to afford protection against homologous and heterologous strains of the virus. To be protective the immunogen(s) should stimulate sufficient mucosal and cell mediated immunity to neutralize and eliminate any FIPV which comes in contact with the cat's immune system.

Known strains of FIPV include:

| | |
|---|---|
| FIPV-UCD1 | Pederson, N C, Boyle, J F, Floyd, K: Infection studies in kittens utilizing feline infectious peritonitis virus propagated in cell culture. Am. J. Vet. Res. 42:363–367, 1981. |
| FIPV-TN406 | Pederson, N C, Black, J W: Attempted immunization of cats against feline infectious peritonitis using either avirulent live virus or sublethal amounts of virulent virus. Am. J. Vet. Res. 44:229–234, 1983. |
| FIPV-79-1146 | Pederson, N C, Evermann, J F, McKeiman, A J, Ott, R L: Pathogenicity studies of feline coronavirus isolates 79-1146 and 79-1683. Am. J. Vet. Res. 45:2580–2585, 1984. |
| FIPV-Nor15 | Evermann, J F, Baumgartner, L, Ott, et al: Characteristics of feline infectious peritonitis virus isolate. Vet. Pathol. 18:256–265, 1981. |
| FIPV-UCD2 FIPV-UCD3 FIPV-UCD4 | Pederson, N C: Experimental studies with three new strains of feline infectious peritonitis virus: FIPV-UCD2, FIPV-UCD3, and FIPV-ECD4. The Comp. Cont. Educ. 7:1001–1011, 1985. |

Feline Coronavirus (enteric) ATCC VR-989. Strain WSU-76–168 (3) (Cross-reacts with FIP NOR 15 strain).

Feline infectious peritonitis (Feline coronavirus) ATCC VR-867 Dahlberg strain.

Feline infectious periotonitis. ATCC VR-990, Strain WSU 79–1146.

Feline infectious peritonitis. ATCC VR-2004, Strain DF2.

Feline infectious peritonitis. ATCC VR-2009, Strain NW-1.

Two types of experiments, in vivo and in vitro tests, can be used to test such vaccines.

For in vitro testing, cats should be vaccinated (twice at an interval of 21 days) with the vaccine and challenged at least twice with the homologous FIPV strain. The cats should be exposed to challenge virus at 14 days post-second vaccination, and be monitored during the post-challenge period for approximately 56 days for clinical symptoms, temperatures, blood pictures (white cell counts, packed cell volumes, and differentials), and death due to challenge exposure. At approximately 56 days post-challenge, the surviving vaccinates and controls, plus naive controls, should be challenged a second time and monitored for 112 days post-initial challenge exposure as described following initial challenge. A second in vivo test should be performed as described above, but using a heterologous FIPV strain as the challenge virus. For a FIPV vaccine to be considered efficacious, it should provide at least a 70% protection rate in the vaccinates against the homologous and heterologous challenge virus strains. For in vitro testing, serum from a vaccinated cat can be used to determine the antigenic relationship of different FIPV strains. Two-fold dilutions of the cat serum are prepared in a microtiter plate. The different FIPV strains are diluted to contain approximately 100 $TCID_{50}$ and an equal volume added to the wells of the diluted serum. The plate is incubated at 37° C. for one week and then examined for viral cytopathic effect (CPE). The serum titer for each FIPV strain is determined as the highest dilution of serum inhibiting CPE. The serum titer for each FIPV strain is compared and should be similar, indicating that the cat serum will neutralize all heterologous FIPV strains equally. This will indicate that the vaccine immunogens are common to all FIPV strains and will protect vaccinated cats against all FIPV strains.

EXAMPLE 5

CrFK (Crandall Feline Kidney) cell line (p 181) was received frozen from the American Type Culture Collection (ATCC). The ampoule containing cells was rapidly thawed in a 37° C. water bath and immediately transferred to a 75 sq. cm flask and 20 ml of Eagle's Minimal Essential Medium with Earle's Salts (MEM-E) and supplemented with 10% heat-inactivated (56° C.) fetal bovine serum, 2 mM L-glutamine, 1% sodium pyruvate and 50 ug/ml gentamicin sulfate (CM). The cells were incubated at 37° C. in a humidified 5% $CO_2$-95% air incubator until confluent.

The cells were passaged at 1:3 split ratios approximately every 3–4 days by detaching cells with a 0.25% trypsin solution. The CM was poured off and the monolayer surface was washed with MEM-E, 3.0 ml of trypsin added, and the monolayer was rocked to flood the cell surface. All but approximately 0.5 ml of trypsin was removed by pipette. After several minutes the cells began to round up and detach from the cell surface. The cells were than resuspended in pre-warmed (37° C.) CM and the cell monolayer was vigorously rinsed and pipetted up and down against the inside of the flask until the cells were released from the cell ground matrix. The suspended cells were divided equally into three separate flasks and incubated at 37° C. This procedure was repeated and at passage 189, a frozen ampoule of the Dahlberg strain of Feline Infectious Peritonitis (FIP), originally isolated from the liver of a cat with infectious peritonitis, received from the ATCC (ATCC VR-867) was rapidly thawed and immersed in ice water. The contents of the ampoule were diluted 1:100 in cold (4 C) MEM-E, and 1.0 ml of the diluted virus was added to each of 3 flasks of CrFK and incubated at 37° C. and observed daily at 200 X magnification with an inverted microscope set on phase contrast illumination.

Five days post-infection (p.i.), syncytia formation was noted and the supernatant was removed from the flasks, pooled and frozen in 1.0 ml aliquots and stored at −85° C. until titrated. Several flasks were trypsinized, cells counted and resuspended in cold CM supplemented with 10% dimethyl sulfoxide (DMSO) as a cryopreservative, and frozen at a controlled rate of freezing at a temperature of 1 degree/minute until frozen, at which time the cells were immersed in liquid nitrogen for storage. Other flasks containing persistently infected cells were filled with CM and further incubated at 37° C. and passaged the same as non-infected cells.

Persistence was monitored by immunofluorescent antibody assay (IFA) and immunoblotting assays (IB). The IFA was used to monitor the cell line for virus or viral antigen production, while the IB was used to detect released virus or viral proteins in the supernatant. Both polyclonal and monoclonal antibodies were employed. Secondary reagents were anti-species IGG conjugated with fluorescein isothiocyanate. Methanol fixed and stained cells were examined with a Nikon fluorescent microscope using epifluorescent microscopy with appropriate barrier and exciter filters. Persistently infected cells were determined as those that emitted specific cytoplasmic apple-green fluorescence.

We determined by changing growth medium conditions and incubation times, that viral proteins were subsequently shed from the persistently infected cells in greater quantities than when normal growth conditions were used. This became the basis for vaccine production. Confluent cell cultures were switched to MEM-E without fetal bovine serum and incubated 72 hours at 37° C. At the end of the incubation period, the supernatants were pooled and concentrated 10 X by dialysis against polyethylene glycol 6000 (PEG6000). The concentrated supernatants were tested for viral antigens initially by a modified Laemmeli immunoblotting technique and positive and negative test supernatants were then treated with detergents to solubilize viral and non-viral proteins and loaded into wells prepared in polyacrylamide slab gels with sodium-dodecyl sulfate (SDS-PAGE).

The material was electrophoresed and transblotted onto a nitrocellulose membrane described by Burnette. The separated proteins were reacted with either polyclonal anti-FIPV serum or monoclonal antibodies to specific viral proteins. The specific-bound immunoglobulins to FIPV were visualized by sequential reactions with goat anti-species (cat or mouse) immunoglobulin-biotin-avidin alkaline phosphatase conjugates and developed in BCIP/NBT phosphatase commercial substrate system.

The Western blotting assay detects separated viral proteins. Coronavirus structural proteins to date have been identified to consist of 6 structural proteins with molecular weights of:

| Acronym | MW | |
|---|---|---|
| S | 180,000 | (Spike glycoprotein) |
| S1 | 90,000 | (N term S cleavage product) |
| S2 | 90,000 | (C-term S cleavage product) |
| HE | 65,000 | (Hemagglutinin-esterase glycoprotein) |
| M | 20–30KD | (Integral membrane protein) |
| N | 50–60KD | (Nucleocapsid protein) |

FIG. 1 shows that the vaccine product produces two of the known viral products with a MW of 30,000 KD (M protein) and one between 50–60,000 MW (N protein). A third as yet unidentified protein with a MW between the M and N proteins was also produced under these experimental conditions. We have seen similar patterns with both the 1146 and Dahlberg strains of FIPV.

The large spike glycoproteins (S, S1 and S2) responsible for membrane fusion and bearing important antigenic sites, varies amazingly in length and composition both within as well as between coronavirus species. Thus, these proteins would not make good vaccines to protect against either homologous or heterologous challenge with FIPV strains. Vennema et al (Vennema, H., DeGroot, R., Harbour, D., Harzinek, M. and Spaan, J. Primary Structure of the membrane and nucleocapsid protein genes of feline infectious peritonitis virus and immunogenicity of recombinant vaccinia viruses in kittens. Virology 181:327–335, (1991))

recombined the fusogenic spike protein of FIPV into the genome of the vaccinia virus, and immunized kittens. The vaccine elicited low titer of neutralizing antibody, but when challenged with virulent virus, died earlier than kittens immunized with the vector strain of viccinia.

The integral member glycoprotein (M) has been shown to use internal hydrophobic sequences to direct translocation within membranes. All Coronaviruses contain the membrane (M) protein which interacts with the nucleocapsid (N). It is involved in virion assembly, and plays a role in determining the site of virus budding from the infected cell. Thus, it would be reasonable to assumed that an FIPV sub-unit vaccine prepared from existing known strains, proprietary strains in private, university and corporate laboratories and as yet to be discovered strains of FIPV, would elicit protective immunity with vaccines prepared with the above described procedures.

Vaccines prepared from any of the above mentioned strains of FIPV following our procedures would be efficacious in protecting immunized kittens against subsequent controlled virulent virus challenge from either homologous or heterologous strains of FIPV. Approximately 80% of FIPV-vaccinated cats would be protected with the predetermined challenge. Since virus load under fetal conditions most likely would be less than challenge doses, immunized kittens may have a greater protection rate than under laboratory conditions.

EXAMPLE 6

The following experiment demonstrated that the vaccine of the present invention protects cats against multiple challenges with DF-2 strain feline infectious peritonitis virus.

The following protocol was followed:

```
10 Cats
  |
Vaccinate
  |
  | 21 days
Vaccinate
  |
  | 14 days
Challenge with DF2
10 Vaccinates
5 controls
  |
1-21 days post-challenge
temperature
clinical observations
14, 28, 42, and 56 days post-challenge
WBC, PCV, differentials
  |
  | 56 days
Challenge
Survivors (vaccinates + controls)
5 naive controls
  |
57-78 post-challenge
temperature
clinical observations
70, 84, 98, and 112 days post-challenge
WBC, PCV, differentials
  |
Terminate at 112 days post-challenge
```

ANIMALS

| Breed/Status: | Harlan Sprague Dawley cats |
|---|---|
| Number: | 40 |
| Age/Sex: | 9-14 weeks |
| Source: | Harlan Sprague Dawley |

EXPERIMENTAL DESIGN

| Groups: | 10 vaccinates 5 controls | |
|---|---|---|
| Key operation dates: | Test Day | Activity |
| | 0 | Bleed/Vaccinate |
| | 21 | Bleed/Vaccinate |
| | 35 | Bleed/Challenge 20 vaccinates 5 controls |
| | 35-36 | Observe/record clinical symptoms WBC, PVC, Diffs |
| | 35 | WBC, PVC, Diffs |
| | 49 | WBC, PVC, Diffs |
| | 63 | WBC, PVC, Diffs |
| | 77 | WBC, PVC, Diffs |
| | 91 | WBC, PVC, Diffs Bleed/Challenge Survivors 5 controls |
| | 91-112 | Observe/record clinical symptoms WBC, PVC, Diffs |
| | 91 | WBC, PVC, Diffs |
| | 105 | WBC, PVC, Diffs |
| | 119 | WBC, PVC, Diffs |
| | 133 | WBC, PVC, Diffs |
| | 147 | WBC, PVC, Diffs |
| | 147 | Terminate |
| Parameters measured: | Clinical symptoms, WBC, PVC, Differentials | |

TEST MATERIALS

| Vaccine: | KV Feline infectious peritonitis virus |
|---|---|
| Vaccination route: | Subcutaneous |
| Dose: | two – 1 ml each |
| Interval: | 21 days |
| Samples: | Blood samples |
| Processing: | Collect serum |
| Storage: | ≦-20° C. |
| Delivery: | Shuttle |
| Challenge: | Virulent challenge virus, DF-2 strain |
| Challenge method: | a. 1.0 ml orally |
| Restraint | Ketamine HCl (5 mg/lb) |

The results are reported in the tables below. Table 3 shows that prior to vaccination each cat in the test group had a negative virus serum neutralization titer, meaning that none had been previously exposed to any strain of feline infectious peritonitis virus or feline enteric coronavirus. Following the second vaccination, but prior to challenge with the virus, all 10 test subjects were producing antibodies to the virus to varying degrees. The antibody titers are very low, which is desirable. It is well known that high antibody responses to vaccination indicate that the cats are sensitized to further exposure to the virus. If the antibody titers had been higher, i.e., 1024 or 2048, this would have indicated a high probability of early death after FIPV challenge. Effective FIPV vaccines appear to operate by a cell mediated immunity mechanism rather than an antibody mediated mechanism. Therefore, columns 3 and 4 of Table 3 are preliminary indications of positive results (i.e., low antibody titers).

TABLE 3

Feline Infectious Peritonitis Virus Vaccine
Immunogenicity Test Dose
Carbopol Adjuvant

| Cat Number | Virus Serum Neutralization Titers* | | |
|---|---|---|---|
| | Pre-Vac | Pre-2nd Vac | Pre-Challenge |
| 110 | NEG | 4 | 128 |
| 112 | NEG | 64 | 128 |
| 114 | NEG | NEG | 128 |
| 118 | NEG | 16 | 256 |
| 126 | NEG | NEG | 2 |
| 132 | NEG | 8 | 128 |
| 141 | NEG | <2 | 4 |
| 163 | NEG | 8 | 16 |
| 173 | NEG | 2 | 128 |
| 175 | NEG | NEG | 8 |

*Virus serum neutralization titers expressed as the highest dilution of serum which caused complete virus neutralization.

Table 4 shows that 8 out of 10 subjects survived the first challenge, i.e., 80% protection. Of the 8 survivors, 7 survived a second challenge, i.e., 87.5% protection.

TABLE 4

Feline Infectious Peritonitis Virus Vaccine
Immunogenicity Test Dose
Carbopol Adjuvant

| Cat Number | Post-Challenge Response | |
|---|---|---|
| | Death | Days Post Challenge |
| DF-2 Challenge - Subcutaneously (First Challenge) | | |
| 110 | + | 27 |
| 112 | (+) | 40* |
| 114 | | |
| 118 | | |
| 126 | | |
| 132 | | |
| 141 | | |
| 163 | | |
| 173 | + | 21 |
| 175 | | |

*Indicates death post second challenge exposure.

TABLE 5

Feline Infectious Peritonitis Virus Vaccine
Immunogenicity Test Dose
Carbopol Adjuvant

| Cat Number | Post-Challenge Response | |
|---|---|---|
| | Death | Days Post Challenge |
| DF-2 Challenge - Subcutaneously (First Challenge) | | |
| 116 | + | 22 |
| 124 | | |

TABLE 5-continued

Feline Infectious Peritonitis Virus Vaccine
Immunogenicity Test Dose
Carbopol Adjuvant

| Cat Number | Post-Challenge Response | |
|---|---|---|
| | Death | Days Post Challenge |
| 129 | (+) | 18* |
| 158 | + | 25 |
| 169 | + | 25 |

*Indicates detach post second challenge exposure.

Table 5 pertains to the original control group and shows that 3 out of 5 unvaccinated cats died after the first challenge. Of the two survivors, one died 18 days after the second challenge with DF-2 FIPV. Three of the 5 naive controls died as a result of exposure to the virus used in the second challenge experiments. This data indicates that the vaccine of the present invention provides significant protection against multiple challenges with a virulent isolate of feline infectious peritonitis virus.

I claim:

1. Feline infectious peritonitis immunogens derived from FIP persistently-infected Crandall feline kidney cells cultured in vitro wherein said FIP immunogens are essentially free of live and dead virus particles.

2. The FIP immunogens of claim 1 harvested from serum-free growth medium.

3. The FIP immunogens of claim 2 wherein said FIP persistently-infected cells are cultured in serum-containing growth medium and then transferred to said serum-free growth medium.

4. The FIP immunogens of claim 1 wherein said cells are from the cell line designated ATCC Accession No. CRL-11137.

5. A method of producing feline infectious peritonitis virus vaccine which is essentially free of live and dead virus particles comprising:

culturing Crandall feline kidney cells persistently infected with FIPV in a serum-containing growth medium, transferring said persistently-infected cells to a serum-free growth medium, separating said persistently-infected cells to recover a supernatant, and inactivating residual live virus in the supernatant.

6. The method of claim 5 wherein said cultured cells are from the cell line designated ATCC Accession No. CRL-11137.

7. The method of claim 5 wherein said supernatant is lyophilized and the resulting powder is recovered.

8. The method of claim 5 wherein said vaccine is diluted with a pharmaceutically-acceptable adjuvant.

9. A vaccine composition for the immunization of FIP-susceptible cats comprising an immunizing-effective amount of supernatant derived from FIP persistently-infected Crandall feline kidney cells cultured in vitro and which is essentially free of live and dead virus particles, has been subjected to a virus inactivation treatment and blended with a pharmaceutically-acceptable adjuvant.

10. The FIP vaccine of claim 9 wherein said persistently-infected cells are cultured in serum-free growth medium.

11. The FIP vaccine of claim 10 wherein said FIP-persistently-infected cells are cultured in serum-containing growth medium and then transferred to said serum-free growth medium.

12. The FIP vaccine of claim 9 wherein said cells are from the cell line designated ATCC Accession No. CRL-11137.

13. A method of immunizing FIP-susceptible cats comprising parenterally inoculating said cat with the vaccine of claim 9.

14. The method of claim 13 wherein said cat is about 6 to 12 weeks of age when inoculated.

15. The method of claim 13 wherein said cat is inoculated with a vaccine derived from the cell line designated ATCC Accession No. CRL-11137.

16. The method of claim 13 wherein said pharmaceutically-acceptable adjuvant is selected from the group consisting of complete or incomplete Freund's adjuvant, aluminum hydroxide, Quil A, EMA, DDA, TDM-Squalene, lecithin, alum, saponin, and mixtures thereof.

17. A Crandall-Kidney cell line persistently infected with FIPV, designated ATCC Accession No. CRL-11137.

* * * * *